(12) United States Patent
Urman et al.

(10) Patent No.: US 11,771,359 B2
(45) Date of Patent: *Oct. 3, 2023

(54) REGION OF INTEREST FOCAL SOURCE DETECTION USING COMPARISONS OF R-S WAVE MAGNITUDES AND LATS OF RS COMPLEXES

(71) Applicant: Biosense Webster (Israel) Ltd., Yokneam (IL)

(72) Inventors: Roy Urman, Karkur (IL); Meir Bar-Tal, Haifa (IL); Yaniv Ben Zrihem, Binyamina (IL); Ziyad Zeidan, Zemmer (IL); Gal Hayam, Tivon (IL); Stanislav Goldberg, Haifa (IL); Atul Verma, Toronto (CA); Yariv Avraham Amos, Tzorit (IL); Richard P. M. Houben, Lanaken (BE)

(73) Assignee: BIOSENSE WEBSTER (ISRAEL) LTD., Yokneam (IL)

(*) Notice: Subject to any disclaimer, the term of this patent is extended or adjusted under 35 U.S.C. 154(b) by 0 days.

This patent is subject to a terminal disclaimer.

(21) Appl. No.: 17/231,612

(22) Filed: Apr. 15, 2021

(65) Prior Publication Data

US 2021/0228138 A1    Jul. 29, 2021

Related U.S. Application Data

(63) Continuation of application No. 15/404,228, filed on Jan. 12, 2017, now Pat. No. 11,006,887.

(Continued)

(51) Int. Cl.
*A61B 5/361* (2021.01)
*A61B 5/00* (2006.01)
(Continued)

(52) U.S. Cl.
CPC .............. *A61B 5/361* (2021.01); *A61B 5/316* (2021.01); *A61B 5/339* (2021.01); *A61B 5/352* (2021.01);
(Continued)

(58) Field of Classification Search
CPC ....... A61B 5/361; A61B 5/352; A61B 5/7275; A61B 5/743; A61B 5/339; A61B 5/316; A61B 5/7239
See application file for complete search history.

(56) References Cited

U.S. PATENT DOCUMENTS 4,945,922 A    8/1990    van Krieken
4,957,118 A    9/1990    Erlebacher
(Continued)

FOREIGN PATENT DOCUMENTS

CN    101156774 A    4/2008
CN    103354730 A    10/2013
(Continued)

OTHER PUBLICATIONS

Neuman, M. R. "Biopotential Electrodes." The Biomedical Engineering Handbook: Second Ed. Joseph D. Bronzino; Boca Raton: CRC Press LLC, 2000 (Year: 2000).*
(Continued)

*Primary Examiner* — Pamela M. Bays
(74) *Attorney, Agent, or Firm* — Volpe Koenig

(57) ABSTRACT

A system and method of identifying focal sources is presented. The method can comprise detecting, via sensors, electro-cardiogram (ECG) signals over time, each ECG signal detected via one of the sensors having a location in a heart and indicating electrical activity of the heart, each signal comprising at least an R wave and an S wave; creating an R-S map comprising an R-to-S ratio for each of the ECG signals, the R-to-S ratio comprising a ratio of absolute (Continued)

magnitude of the R wave to absolute magnitude of the S wave; identifying, for each of the ECG signals, local activation times (LATs); and correlating the R-to-S ratios for the ECG signals on the R-S map and the identified LATs and using the correlation to identify the focal sources.

19 Claims, 7 Drawing Sheets

Related U.S. Application Data

(60) Provisional application No. 62/278,676, filed on Jan. 14, 2016.

(51) Int. Cl.
*A61B 5/316* (2021.01)
*A61B 5/352* (2021.01)
*A61B 5/339* (2021.01)
*A61B 18/14* (2006.01)
*A61B 5/287* (2021.01)
*A61B 5/366* (2021.01)

(52) U.S. Cl.
CPC .......... *A61B 5/7239* (2013.01); *A61B 5/7275* (2013.01); *A61B 5/743* (2013.01); *A61B 5/287* (2021.01); *A61B 5/366* (2021.01); *A61B 18/1492* (2013.01); *A61B 2562/046* (2013.01)

(56) References Cited

U.S. PATENT DOCUMENTS

| | | | |
|---|---|---|---|
| 5,257,634 A | 11/1993 | Kroll | |
| 5,300,107 A | 4/1994 | Stokes et al. | |
| 5,680,860 A | 10/1997 | Imran | |
| 5,938,694 A | 8/1999 | Jaraczewski et al. | |
| 5,968,040 A | 10/1999 | Swanson et al. | |
| 6,216,043 B1 | 4/2001 | Swanson et al. | |
| 6,529,756 B1 | 3/2003 | Phan et al. | |
| 6,684,109 B1 | 1/2004 | Osypka | |
| 6,917,834 B2 | 7/2005 | Koblish et al. | |
| 6,973,339 B2 | 12/2005 | Govari | |
| 8,433,398 B2 | 4/2013 | Zhang | |
| 8,454,594 B2 | 6/2013 | Demarais et al. | |
| 9,283,381 B2 | 3/2016 | Grubac et al. | |
| 9,750,422 B2 | 9/2017 | Zino et al. | |
| 10,112,045 B2 | 10/2018 | Anderson et al. | |
| 2002/0022839 A1 | 2/2002 | Stewart et al. | |
| 2002/0055674 A1 | 5/2002 | Ben-Haim et al. | |
| 2002/0123694 A1 | 9/2002 | Organ et al. | |
| 2002/0183638 A1 | 12/2002 | Swanson | |
| 2003/0093004 A1 | 5/2003 | Sosa et al. | |
| 2003/0093072 A1 | 5/2003 | Friedman | |
| 2004/0059237 A1* | 3/2004 | Narayan | A61B 5/35 607/9 |
| 2004/0243012 A1 | 12/2004 | Ciaccio et al. | |
| 2005/0038333 A1 | 2/2005 | Sra | |
| 2005/0288730 A1 | 12/2005 | Deem et al. | |
| 2006/0085054 A1 | 4/2006 | Zikorus et al. | |
| 2007/0083193 A1 | 4/2007 | Werneth et al. | |
| 2007/0083195 A1 | 4/2007 | Werneth et al. | |
| 2007/0197929 A1 | 8/2007 | Porath et al. | |
| 2008/0188765 A1 | 8/2008 | Stolarski et al. | |
| 2008/0281322 A1 | 11/2008 | Sherman et al. | |
| 2009/0112199 A1 | 4/2009 | Zhang et al. | |
| 2009/0253974 A1 | 10/2009 | Rahme | |
| 2009/0299447 A1 | 12/2009 | Jensen et al. | |
| 2011/0054560 A1 | 3/2011 | Rosenberg et al. | |
| 2011/0125041 A1* | 5/2011 | Fischell | A61B 5/364 600/515 |
| 2011/0230775 A1 | 9/2011 | Barley et al. | |
| 2011/0251505 A1 | 10/2011 | Narayan et al. | |
| 2012/0232417 A1* | 9/2012 | Zhang | A61B 5/7282 600/521 |
| 2013/0006131 A1 | 1/2013 | Narayan et al. | |
| 2013/0116681 A1 | 5/2013 | Zhang | |
| 2013/0131746 A1* | 5/2013 | Simon | A61N 1/3625 607/9 |
| 2013/0274582 A1 | 10/2013 | Afonso et al. | |
| 2014/0005563 A1 | 1/2014 | Ramanathan et al. | |
| 2014/0052118 A1 | 2/2014 | Laske et al. | |
| 2014/0052208 A1 | 2/2014 | Ransbury et al. | |
| 2014/0081114 A1 | 3/2014 | Shachar et al. | |
| 2014/0130059 A1 | 5/2014 | Goodman | |
| 2014/0296850 A1 | 10/2014 | Condie et al. | |
| 2014/0336520 A1 | 11/2014 | Zeng et al. | |
| 2015/0051682 A1 | 2/2015 | Schmidt et al. | |
| 2015/0216435 A1 | 8/2015 | Bokan et al. | |
| 2015/0216438 A1 | 8/2015 | Bokan et al. | |
| 2015/0342676 A1 | 12/2015 | McCarthy et al. | |
| 2015/0351652 A1 | 12/2015 | Marecki et al. | |
| 2016/0045123 A1* | 2/2016 | Bar-Tal | A61B 5/287 600/515 |
| 2016/0183824 A1 | 6/2016 | Severino | |
| 2016/0302858 A1 | 10/2016 | Bencini | |
| 2017/0065818 A1 | 3/2017 | Ransbury et al. | |
| 2017/0251978 A1 | 9/2017 | Rodrigo Bort et al. | |
| 2018/0161577 A1 | 6/2018 | Goedeke et al. | |

FOREIGN PATENT DOCUMENTS

| | | |
|---|---|---|
| CN | 103584852 A | 2/2014 |
| EP | 2 984 986 A2 | 2/2016 |
| WO | 2016/038237 A1 | 3/2016 |
| WO | 2017/024107 A1 | 2/2017 |

OTHER PUBLICATIONS

Allessie et al., "Electropathological substrate of long standing persistent atrial fibrillation in patients with structural heart disease: Longitudinal Dissociation," Circulation—Arrhythmia and Electrophysiology, pp. 606-615 (Dec. 2010).

De Groot et al., "Electropathological Substrate of Longstanding Persistent Atrial Fibrillation in Patients With Structural Heart Disease: Epicardial Breakthrough," Circulation, pp. 1674-1682 (Oct. 26, 2010).

Houben et al., "S-wave predominance of epicardial electrograms during atrial fibrillation in humans: Indirect evidence for a role of the thin subepicardial layer," Heart Rhythm, vol. 1, No. 6, pp. 639-647 (Dec. 2004).

Inoue et al., "Trigger-based mechanism of the persistence of atrial fibrillation and its impact on the efficacy of catheter ablation," Circulation—Arrhythmia and Electrophysiology, pp. 295-301 (Apr. 2012).

Lee et al., "Simultaneous Bi-Atrial High Density (510-512 Electrodes) Epicardial Mapping of Persistent and Longstanding Persistent Atrial Fibrillation in Patients: New Insights into the Mechanism of Its Maintenance," Circulation, vol. 132, Issue 22, pp. 2108-2117 (Dec. 1, 2015).

Narayan, et al. "Classifying Fractionated Electrograms in Human Atrial Fibrillation Using Monophasic Action Potentials and Activation Mapping: Evidence for Localized Drivers, Rate Acceleration, and Nonlocal Signal Etiologies", Heart Rhythm, Elsevier, US, vol. 8, No. 2, Oct. 11, 2010, pp. 244-253.

Houben, et al. "S-Wave Predominance of Epicardial Electrograms During Atrial Fibrillation in Humans: Indirect Evidence for a Role of the Thin Subepicardial Layer," Heart Rhythm, Elsevier, US, vol. 1, No. 6, Dec. 1, 2004, pp. 639-647.

Communication Pursuant to Article 94(3) EPC dated Aug. 28, 2018 for the European Patent Application No. 17151634.7.

Communication Pursuant to Article 94(3) EPC dated Aug. 28, 2018 for the European Patent Application No. 171516255.

Extended European Search Report dated May 18, 2017 for the European Patent Application No. 17151625.5.

Extended European Search Report dated May 26, 2017 for the European Patent Application No. 17151629.7.

Chinese Office Action dated Oct. 9, 2020 for Chinese Patent Application No. 201710032337.4.

(56) References Cited

OTHER PUBLICATIONS

Karimifard S, Ahmadian A., "Morphological heart arrhythmia classification using Hermitian model of higher-order statistics," Annu Int Conf IEEE Eng Med Biol Soc. 2007;2007:3132-5. doi: 10.1109/IEMBS.2007.4352993. PMID: 18002659.

* cited by examiner

REGION OF INTEREST FOCAL SOURCE DETECTION USING COMPARISONS OF R-S WAVE MAGNITUDES AND LATS OF RS COMPLEXES

CROSS REFERENCE TO RELATED APPLICATION(S)

This application is a continuation of U.S. patent application Ser. No. 15/404,228, filed Jan. 12, 2017, now issued as U.S. Pat. No. 11,006,887, which claims the benefit of U.S. Provisional Application No. 62/278,676, filed Jan. 14, 2016, which is incorporated by reference as if fully set forth. This application incorporates by reference as if fully set forth U.S. patent application Ser. No. 15/404,225 titled "Region of Interest Rotational Activity Pattern Detection," now issued as U.S. Pat. No. 10,582,894, U.S. patent application Ser. No. 15/404,244 titled "Identification of Fractionated Signals", now issued as U.S. Pat. No. 10,314,542, U.S. patent application Ser. No. 15/404,226 titled "Overall System and Method for Detecting Regions of Interest," U.S. patent application Ser. No. 15/404,231 titled "Non-Overlapping Loop-Type or Spline-Type Catheter To Determine Activation Source Direction and Activation Source Type," now issued as U.S. Pat. No. 10,624,554, and U.S. patent application Ser. No. 15/404,266 titled "Region of Interest Focal Source Detection," now issued as U.S. Pat. No. 10,517,496, all filed on Jan. 12, 2017. This application also incorporates by reference as if fully set forth U.S. patent application Ser. No. 16/836,718 titled "Non-Overlapping Loop-Type or Spline-Type Catheter To Determine Activation Source Direction and Activation Source Type," filed on Mar. 31, 2020.

FIELD OF INVENTION

The present invention relates the field of medical diagnosis and treatment, particularly as it pertains to atrial fibrillation. In particular, the present invention relates to systems and methods for determining regions of interest to be ablated for treatment of cardiac arrhythmia, such as atrial fibrillation, and, more particularly, to systems and methods for determining atrial fibrillation regions of interest to be ablated using maps representing detected electrical activity of the heart and maps representing spatio-temporal manifestations of the conditions indicative of the electrical activity of the heart.

BACKGROUND

Cardiac arrhythmia includes different types of abnormal or irregular heart rhythms, such as, for example, atrial fibrillation (AF), which is characterized by rapid and irregular beating. Under normal heart conditions, a heartbeat is produced by electrical pulses (i.e., signals) which originate in the upper chambers (i.e., atria) of the heart and pass through the atria through the atrioventricular (AV) node to a pair of lower chambers (i.e., ventricles) of the heart. As the signals pass through the atria, the atria contract and pump blood from the atria into the ventricles. As the signals pass through the AV node to the ventricles, the ventricles are caused to contract, pumping out blood from the heart to the body. During conditions of AF, however, the signals in the atria become chaotic and cause the heart to beat irregularly.

AF can negatively affect the physical, psychological and emotional quality of a person's life. AF can progressively increase in severity and frequency and, if left untreated, may lead to chronic fatigue, congestive heart failure or stroke. One type of AF treatment includes prescribed medications, such as rhythm control medications and medications used to manage the increased risk of stroke. These medications must be taken daily and indefinitely. Another type of AF treatment includes cardioversion, which attempts to restore a normal heart rhythm by providing electric shocks to the heart through electrodes placed on the chest. In some persistent types of AF, cardioversion is either ineffective or cannot be attempted.

Recent approaches for treating AF include minimally invasive ablation procedures (e.g., catheter ablation) in which the heart tissue is ablated to selectively terminate electrical pathways and block faulty electrical impulses that can cause heart rhythm disorders.

For example, a study for characterizing the morphology of fibrillation electrograms in patients in order to provide insight into the underlying electropathologic substrate of atrial fibrillation (AF) was published by Houben, Richard P M, et al. "S-wave predominance of epicardial electrograms during atrial fibrillation in humans: indirect evidence for a role of the thin subepicardial layer." Heart Rhythm 1.6 (2004): 639-647; which is incorporated herein by reference. In addition, Allessie, Maurits A., et al. "Electropathological substrate of long-standing persistent atrial fibrillation in patients with structural heart disease longitudinal dissociation." Circulation: Arrhythmia and Electrophysiology 3.6 (2010): 606-615, which is incorporated herein by reference, describes epicardial mapping of the right atrium, the left lateral wall, and the posterior left atrium during cardiac surgery, in 24 patients with long-standing persistent AF.

Also, de Groot, Natasja M S, et al. "Electropathological Substrate of Longstanding Persistent Atrial Fibrillation in Patients With Structural Heart Disease Epicardial Breakthrough." Circulation 122.17 (2010): 1674-1682, which is incorporated herein by reference, describes high-density mapping of the right and left atria during cardiac surgery in 24 patients with longstanding persistent AF and structural heart disease. Even though the problem has been studied, the current methods of detection and treatment fall far short of providing appropriate regions of interest for ablation.

SUMMARY

A system and method of identifying focal sources can comprise detecting, via a plurality of sensors, electro-cardiogram (ECG) signals over time, each ECG signal detected via one of the plurality of sensors having a location in a heart and indicating electrical activity of the heart, each signal comprising at least an R wave and an S wave; creating an R-S map comprising an R-to-S ratio for each of the plurality of ECG signals, the R-to-S ratio comprising a ratio of absolute magnitude of the R wave to absolute magnitude of the S wave; identifying, for each of the plurality of ECG signals, one or more local activation times (LATs); and correlating the R-to-S ratios for one or more of the plurality of ECG signals on the R-S map and the identified LATs and using the correlation to identify the focal sources.

In one aspect the method can further comprise calculating a derivative for each of the R-S ratios; and identifying an earliest activation LAT having largest negative value of the calculated derivative of the R-S ratio.

In one aspect, the method can further comprise determining, from the plurality of ECG signals, a strongest ECG signal having a largest difference between the magnitude of the R wave and the magnitude of the S wave, and a location of the sensor having the strongest ECG signal, wherein at least one of the focal sources is identified as the location of the sensor having the strongest ECG signal and the earliest activation LAT.

In one aspect, the method can further comprise displaying, on a display device, the R-S map and the LATs; and representing the identified focal source using a suitable property selected from the group of color, texture and size.

In one aspect, the method can further comprise determining a dominant focal source from the identified focal sources.

In one aspect, the method can further comprise comparing cycle lengths of each of the identified focal sources with temporally-corresponding cycle lengths of arrhythmic heartbeat signal; and determining the dominant focal source as the identified focal source having the cycle length corresponding most closely to the temporally-corresponding cycle length of the arrhythmic heartbeat.

A system for identifying focal sources can comprise a plurality of sensors each configured to detect one of a plurality of electro-cardiogram (ECG) signals over time each having a location in a heart and indicating electrical activity of the heart, each signal comprising at least an R wave and an S wave; a processing device comprising one or more processors configured to: create an R-S map comprising an R-to-S ratio for each of the plurality of ECG signals, the R-to-S ratio comprising a ratio of absolute magnitude of the R wave to absolute magnitude of the S wave; identify, for each of the plurality of ECG signals, one or more local activation times (LATs); and correlate the R-to-S ratios for one or more of the plurality of ECG signals on the R-S map and the identified LATs and using the correlation to identify the focal sources.

A computer program product for identifying focal sources is also presented.

BRIEF DESCRIPTION OF THE DRAWINGS

A more detailed understanding can be had from the following description, given by way of example in conjunction with the accompanying drawings wherein.

DETAILED DESCRIPTION

Conventional methods and systems used for catheter ablation typically include inserting the catheter through an incision in the skin and guided up to the heart. Before ablation is performed, intra-cardiac electrocardiogram (IC ECG) signals of the heart are acquired via electrodes placed at different areas of the heart. The signals are monitored and used to provide information to determine whether one or more areas of the heart are causing the irregular heart rhythm. The conventional methods and systems used to determine these areas to be ablated, however, are time consuming (e.g., several hours) and rely on medical personnel with specific expertise and experience, (typically requiring many hours of training).

Embodiments disclosed herein employ systems, apparatuses and methods of determining potential regions of interest (ROIs) to be targeted for ablation. Various mapping techniques are utilized to provide maps of the electrophysical conditions of the AF substrate and maps representing a spatio-temporal manifestation of the AF process to provide efficient and accurate determination of potential ablation ROIs. Mapping techniques utilize various parameters (e.g., cycle, earliness, R-S complex, conduction velocity (CV), block and fractionation) of acquired IC ECG signals and detected local activation times (LATs) to identify potential evidence of drivers and perpetuators of the AF substrate. Identification of the potential evidence of drivers and perpetuators is used to provide mapping (e.g., driver maps and perpetuator maps) of the AF substrate. Mapping techniques also include utilizing the various parameters of the acquired IC ECG signals and detected local activation times to provide mapping (e.g., activation/wave maps, CV maps, fractionation maps, voltage maps and block maps) which potentially represents the spatio-temporal manifestation of the AF process. The mapping of the spatio-temporal manifestation of the AF process can be used in addition to, or alternative to, the mapping of the AF substrate to identify potential ablation ROIs. The mapping techniques are used to potentially reduce AF map analysis training time, increase success rates resulting from ablation and facilitate efficient interpretation of AF maps. For simplification purposes, embodiments described herein refer to systems and methods used for the treatment of AF. It is noted however, embodiments may be used for the treatment of any type of cardiac arrhythmia including different types of abnormal or irregular heart rhythms.

Figure 1:
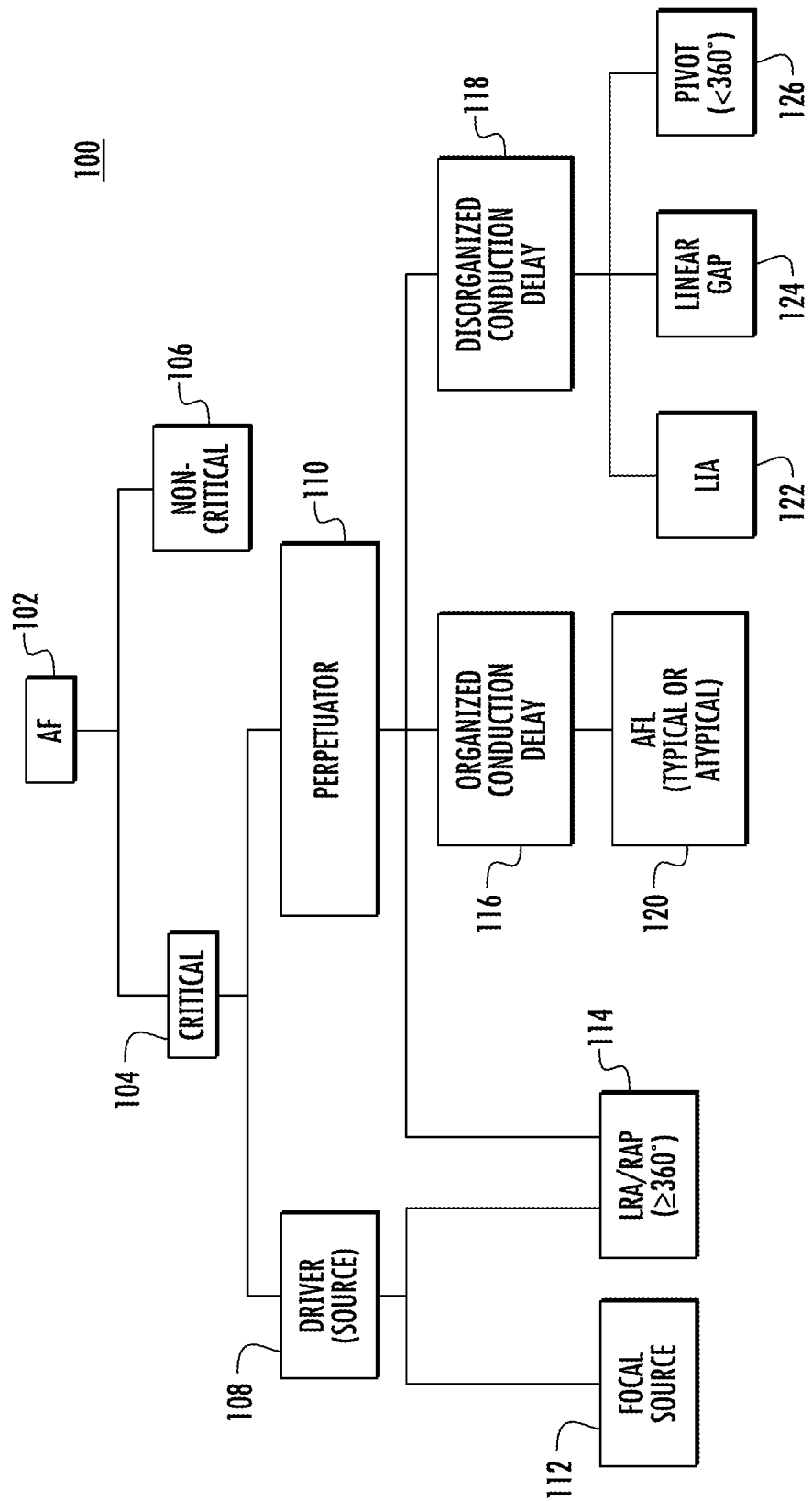
FIG. 1 is a block diagram illustrating an exemplary classification of AF used with embodiments disclosed herein.

FIG. 1 is a block diagram illustrating an exemplary classification of AF used with embodiments disclosed herein. The exemplary classification in FIG. 1 distinguishes between critical and non-critical AF as well as between drivers and perpetuators of AF and their relative spatio-temporal patterns.

For example, as shown in FIG. 1, an irregular heart rhythm characterized as AF 102 is classified as critical 104 or non-critical 106. Examples of non-critical AF 106 include paroxysmal (i.e., intermittent) irregular heart rhythm episodes in which the heartbeat often normalizes as quickly as within a few seconds or after a few hours, and persistent irregular heart rhythm episodes in which a normal heart may be restored by rhythm medical therapy or a procedure (e.g., cardioversion). Examples of critical AF 104 include long-standing persistent irregular heart rhythm episodes that continue for longer periods of time (e.g., more than a year) in which the heart is in a constant state of AF and the condition is considered permanent.

Critical AF can be classified according to characteristics (e.g., areas of activation) that can be derived from IC ECG signals. Areas of activation may be identified as potential contributing factors to AF. As shown in FIG. 1, critical AF is classified according to different areas of activation, including a potential driver of AF (hereinafter "driver") or potential source of AF (hereinafter "source") 108 and a potential perpetuator 110 of AF (hereinafter "perpetuator"). A driver 108 is an area of activation (e.g., in the atria) where electrical pulses originate to stimulate the heart to contract and which can potentially contribute to AF, for example, by producing fibrillatory conduction to other areas of the atria. A perpetuator 110 is an area of sustained activation (e.g., electrophysiological process/substrate) which can also potentially contribute to AF.

Drivers 108 and perpetuators 110 may be represented (e.g., mapped) according to their spatio-temporal manifestation. As shown in FIG. 1, drivers 108 and perpetuators 110 are classified by exemplary spatio-temporal manifestation types, including focal sources (foci) 112 and localized rotational activation (LRA) sources or rotational activation patterns (RAPs) sources 114. A focal source is a type of driver originating at a small area of the atria which spreads centrifugally from a single point. A RAP 114 source is an irregular region of the heart where the electrical pulses rotate at least 360 degrees about a center area.

FIG. 1 also shows different types of perpetuators 110, including one type which exhibits organized conduction delay 116 and another which exhibits disorganized conduction delay 118. Another type of perpetuator 110 shown in FIG. 1 includes atrial flutter (AFL) 120, characterized by organized conduction delay 116 as well as localized irregular activation (LIA) 122, linear gaps 124 and pivots 126 (i.e., electrical pulses that rotate less than 360 degrees about a center area), characterized by disorganized conduction delay 118. Also, the RAP source 114 is shown as both a driver 108 and a perpetuator 110. Drivers 108 and perpetuators 110 are, for example, separately mapped to facilitate identification of driver types and/or perpetuator types and provide efficient and accurate determination of potential ablation ROIs.

Mapping and identification of drivers 108 and perpetuators 110 can also be based on one or more additional factors which may potentially contribute to AF or parameters which may potentially characterize the AF substrate (i.e., the AF process itself) and/or the manifestation of the AF process. For example, AF parameters or AF factors used to identify potential focal sources 108 include omnidirectional activation spread of activation from a point, earliness (e.g., focal source which starts after an excitable gap), triggers such as fast firing (e.g., short cycle-length and high dominant frequency) foci and breakthroughs (e.g., pulmonary veins (PV), free wall and transmural, endocardial and epicardial) and micro re-entry circuit which manifests as focal source and short-radius re-entry circuits which can manifest as a driver 108 depending on the specific anisotropic structure of the central obstacle.

AF parameters or AF factors used to map and identify RAP sources 114 include, for example, repetitive cycles, rotors which can manifest as a driver source 108, structural or functional anisotropy (e.g., localized or distributed), and short-radius re-entry circuits which can manifest as either a driver 108 or a perpetuator 110, depending on specific anisotropic structure of the central obstacle.

AF parameters or AF factors used to map and identify perpetuators 110 include, for example, extension (increased) path length, anatomical (pathological) block lines, fibrosis, stable functional block lines (e.g., areas of prolonged refractoriness), criticality (e.g., shortest path around block line>path length) and fibrillatory conduction factors (e.g., dissociated waves, re-entry circuit factors).

Figure 2:
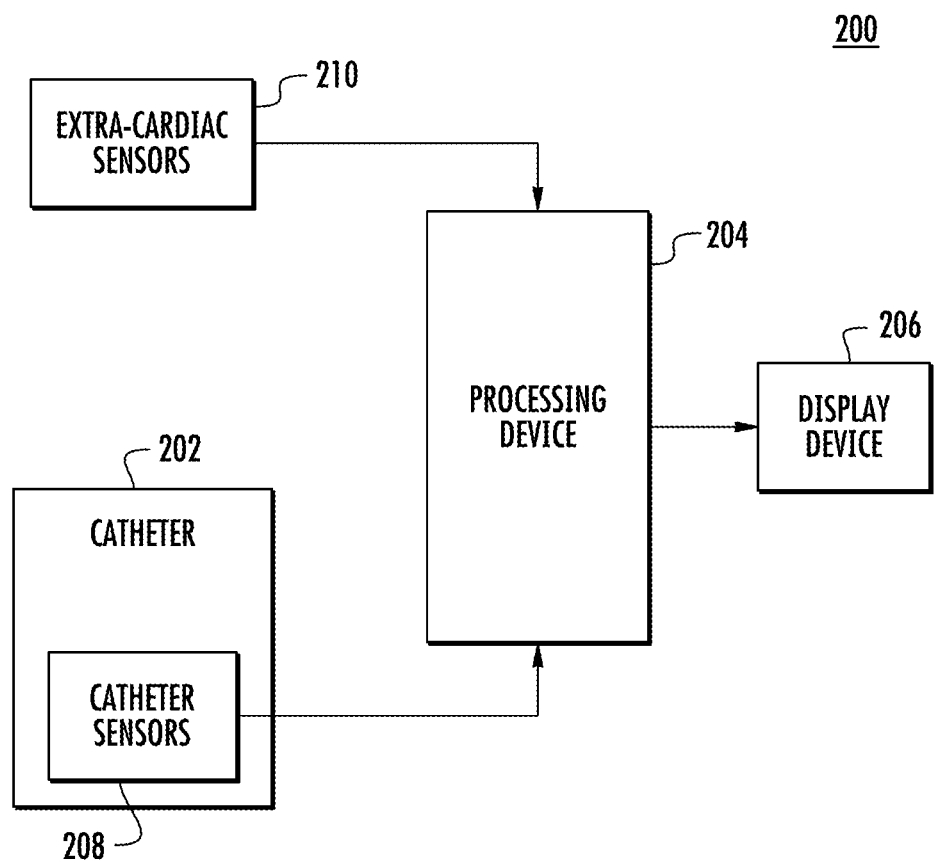
FIG. 2 is a block diagram illustrating an exemplary system used to determine AF ROIs for ablation for use with embodiments disclosed herein.

FIG. 2 is a block diagram illustrating an exemplary system 200 used to determine AF ROIs for ablation for use with embodiments disclosed herein. As shown in FIG. 2, the system 200 includes a catheter 202, a processing device 204 and a display device 206. Catheter 202 includes an array of catheter sensors (e.g., electrodes) each configured to detect electrical activity (electrical signals) of an area of the heart over time. When an IC ECG is performed, each electrode detects the electrical activity of an area of the heart in contact with the electrode. The system 200 also includes extra-cardiac sensors 210 (e.g., electrodes on the skin of a patient) configured to detect electrical activity of the heart via detection of electrical changes on the skin due to the electro-physiologic pattern of the heart.

The detected IC ECG signals and the detected extra-cardiac signals are processed (e.g., recorded over time, filtered, fractionated, mapped, combined, interpolated, etc.) by processing device 204 and displayed on display device 206.

Embodiments may include any number of sensors 210 used to detect ECG signals, including sensors used to detect IC ECG signals and extra-cardiac ECG signals. For simplification purposes, systems and methods described herein refer to the detection and use of IC ECG signals. It is noted, however, that embodiments may utilize IC ECG signals or extra-cardiac ECG signals or a combination of both IC ECG signals and extra-cardiac ECG signals.

Processing device 204 may include one or more processors each configured to process the ECG signals. Each processor of processing device 204 may be configured to record ECG signals over time, filter ECG signals, fractionate ECG signals into signal components (e.g., slopes, waves, complexes), map ECG signals, combine ECG signal information, map and interpolate mapping information, etc.

Display device 206 may include one or more displays each configured to display ECG signals, ECG signal information, maps of the AF process and maps representing a spatio-temporal manifestation of the AF process.

The catheter sensors 208 and the extra cardiac sensors 210 may be in wired or wireless communication with processing device 204. Display device 206 may also be in wired or wireless communication with processing device 204.

Figure 3A:
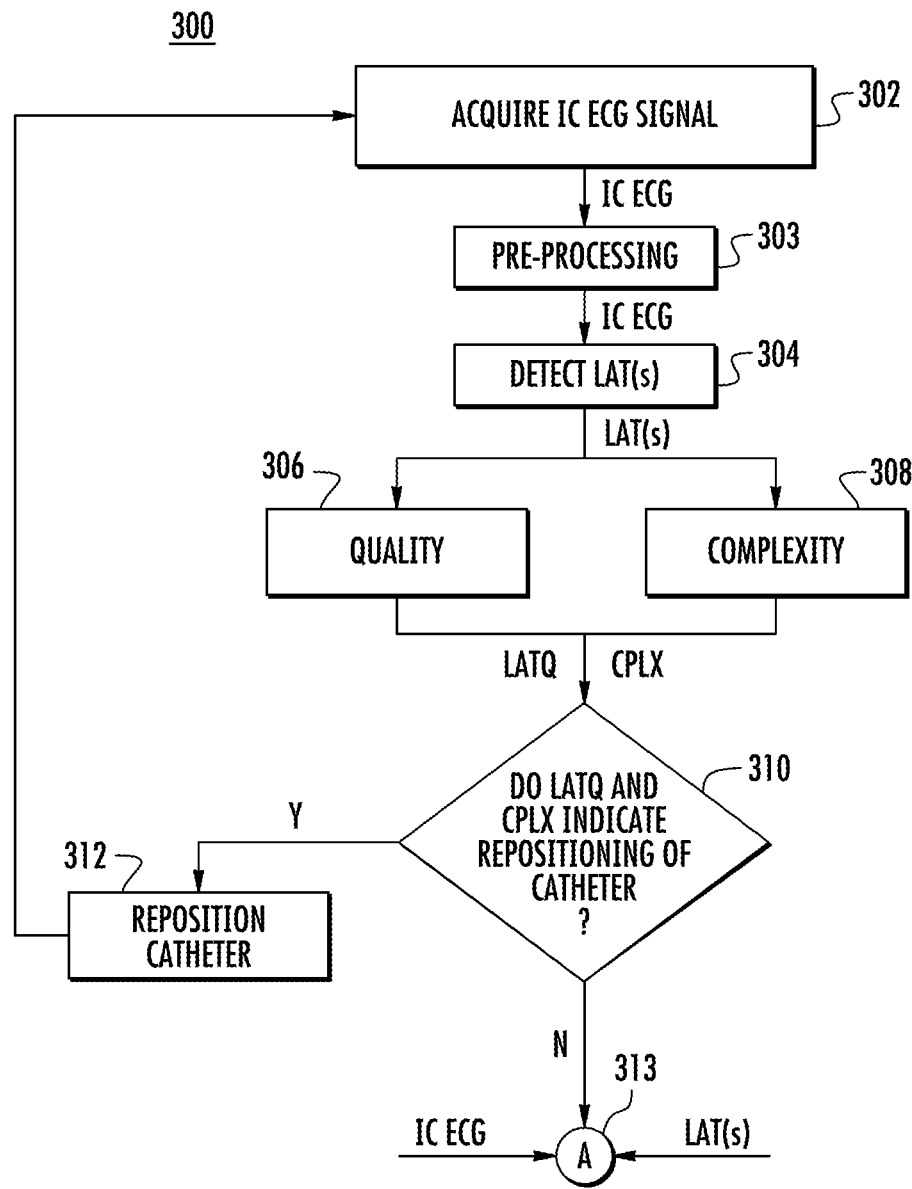
FIGS. 3A and 3B are portions of a flow diagram illustrating an exemplary method of determining an AF ROI for ablation according to an embodiment.
Figure 3B:
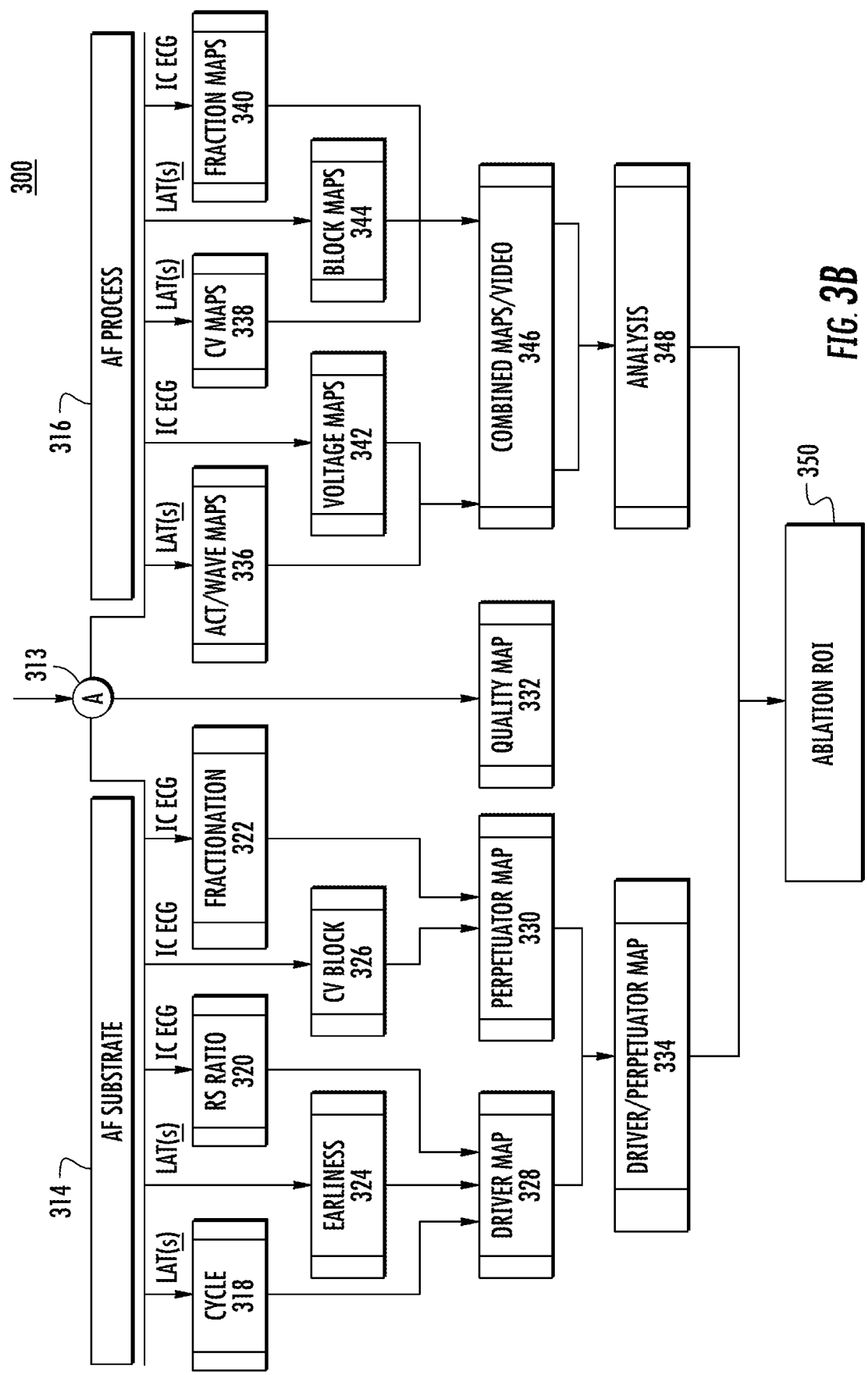

FIGS. 3A and 3B are portions of a flow diagram illustrating an exemplary method 300 of determining a potential ablation ROI. The method 300 employs a mapping taxonomy which includes, from its core moving outward, an IC ECG layer, a pre-processing layer, a LAT detection layer, a map segmentation layer, a map interpolation layer and a map interpretation layer.

FIG. 3A illustrates a portion of exemplary method 300. As shown in block 302 of FIG. 3A, the method 300 includes, as part of the IC ECG layer, acquiring an IC ECG signal which represents electrical activity of an area of the heart. The IC ECG signal acquired at block 302 is, for example, acquired from one of a number of electrodes in contact with different areas of the heart. After acquisition of the IC ECG (302), the method 300 includes, as part of the pre-processing layer, pre-processing of the acquired ECG signal, as shown in block 302 of FIG. 3A, The pre-processing may include execution of one or more algorithms, such as for example, cancellation of ventricular far field signals, baseline correction, and noise reduction. Ventricular far field detection may include, for example, a spatial averaging method (SAM), a temporal averaging method (TAM), a system identification method (SIM) and principal component analysis (PCA).

For each IC ECG signal acquired at block 302, one or more LATs of the corresponding pre-processed IC ECG signal is (are) detected at block 304. The LAT quality (shown as LATQ in FIG. 3A) of each signal is determined at block 306 as part of an exemplary LAT detection layer. The AF complexity (shown as CPLX in FIG. 3A) of the signal is determined at block 308.

As shown at decision point 310, the method 300 includes determining whether to reposition the catheter based on the LAT quality of the signal and the AF complexity. A typical characteristic of high quality IC ECGs is little base line wander (e.g., low baseline vs. IC ECG RMS amplitude, limited ventricular far-field potentials vs. IC ECG RMS amplitude). IC ECG signals characteristics include discernable atrial complexes (e.g., confined (~50 ms) complexes separated by isoelectric segments repeating slopes, 50-200 ms interval; about 150 ms median) during AF. High quality complexes characteristic typically have considerable amplitudes and steep downward slopes (vs. upward slopes) within complexes. Characteristics of the IC ECG signals may be combined into a single measurable characteristic or parameter (e.g., having a measurable value of 0%-100%) to define LAT quality. The LAT quality may be compared to the AF complexity to determine whether to reposition the catheter.

In some embodiments, quality is defined by an ability to map AF for a level of AF complexity. Determining whether to reposition the catheter may include generating a map and determining whether the generated map can be used (e.g., is adequate) to map AF based on whether a level of coverage of a mapping electrode meets (e.g., matches) a level of AF complexity. The ability to map AF for a level of AF complexity may include meeting a map threshold level (e.g., adequate level, trustworthy level). A single parameter (i.e., mapping coverage) is used to define a level of coverage of the mapping electrode. Examples of characteristics that are combined to define the mapping coverage include: (1) contact of the mapping electrode (e.g., contact with active tissue (wall) related to covered area and LAT accuracy); (2) resolution of the electrodes (e.g., distances and electrode sensitivity radii between electrodes, including mean, minimum and maximum and distances); and (3) quality of the IC ECG and associated annotations provided by a detection algorithm.

AF complexity may include complexity of activation during AF creating wave dissociation (block lines), fusion and wave curvature. Accordingly, a map may be determined as a map which can be used (e.g., trustworthy or adequate) to map AF when, given a certain level of AF complexity (e.g., measured along y-axis), the mapping coverage (including signal and annotation quality measured along x-axis) is sufficient to map the AF complexity. If not, the trustworthiness of the map may become compromised or inadequate.

Signals may then be analyzed using the trustworthy or adequate maps to determine whether the catheter should be repositioned. If it is determined at decision point 310 to reposition the catheter, the catheter (e.g., catheter 202) is repositioned at block 312 and a new IC ECG signal is acquired at block 302. If it is determined at decision point 310 that the catheter should be repositioned, the method 300 continues to "point A" 313 (shown in FIG. 3A and FIG. 3B).

FIG. 3A illustrates the acquiring of a single IC ECG signal for simplification purposes. In practice, however, multiple signals are acquired for each of the plurality of electrodes contacting the heart. Each IC ECG signal acquired at block 202 and the one or more LATs detected for each signal at block 204 are received at "point A" 313.

FIG. 3B illustrates exemplary methods which may be used to determine potential ablation ROIs. As shown FIG. 3B, each acquired IC ECG signal and the one or more detected LATs for each signal are used to generate maps of the AF process that includes the electro-physical conditions of the AF substrate (indicated as the AF Substrate 314 in FIG. 3B) and maps representing a spatio-temporal manifestation of the AF process (indicated as the AF Process 316 in FIG. 3B) as part of an exemplary map segmentation layer.

For example, with regard to the AF Substrate 314 shown in FIG. 3B, the one or more detected LATs are used to independently determine one or more factors or parameters which may contribute to AF. The left side of FIG. 3B illustrates methods which characterize the AF substrate by collecting information over a predefined window of time while assessing a mean interval (e.g., cycle) based on a difference of subsequent LATs 318, first activated (earliness) 324, and morphological aspects of the IC ECG including RS-ratio 320 and fractionation 322 (e.g., fractionated electrograms). For example, the detected LATs are used to independently determine cycle information (e.g., cycle lengths) at block 318 and earliness information (e.g., earliest activation times, early drivers which start after an excitable gap) at block 324. Each IC ECG signal is also used to independently determine R-S complex information (e.g., ratio of R wave to S wave) at block 320 and information obtained by fractionation (e.g., slope information, information indicating an incidence of source behavior presented as the earliest activation from one of a plurality of electrodes, such as showing a percentage that the associated electrode was activated earlier than neighbouring electrodes) of the IC ECG signals at block 322 and CV Block information (e.g., information indicating slowed or blocked conduction (i.e., progression) of electrical impulses through the heart, such as the conduction time (CT) for the electrical pulse to travel a distance in the heart, the path length (i.e., the distance) and the CV of the electrical pulse) at block 326.

As shown, a driver map 328 is generated from the cycle information 318, the earliness information 324 and the R-S complex information 320. A perpetuator map 330 is generated from the CV Block information 326 and the fractionation information 322. As shown, the information used to generate the driver map 328 and the information used to generate the perpetuator map 330 are combined (e.g., a single map, overlaid maps or adjacent maps in one display area) to generate a combined driver/perpetuator map 334. The combined driver/perpetuator map 334 may then be used (e.g., interpolated as part of an exemplary map interpolation layer) to determine one or more ablation ROIs 350.

With regard to the AF Process 316 shown in FIG. 3B, the one or more detected LATs are used to independently generate activation/wave maps 336, CV maps 338 (e.g., maps generated from the CT, the path length and/or the CV of the electrical pulse) and block maps 344 (e.g., maps generated from information indicating a block in the conduction of the signal).

Activation/wave maps 326 may, for example, include a map representing an incidence of source behavior presenting the earliest activation of one of a plurality of electrodes restricted by the same wave, such as indicating a percentage of activation waves detected by a corresponding electrode activated earlier than neighboring electrodes though restricted by neighbors activated by the same wave. Activation/wave maps 326 may, for example, also include a map representing the incidence of electrode positions associated with a fibrillation wave start.

Each IC ECG signal is used to independently generate voltage maps 342 and fraction maps 340. The information used to generate maps 336-344 is combined to provide combined maps or video 346. In some embodiments, the information used to generate the activation/wave maps 336 and Voltage maps 342 is combined to generate a combined activation/wave/voltage map or video and the information used to generate the CV maps 338, the block maps 344 and the fraction maps 340 are combined to generate a combined CV/block/fraction map or video. The combined maps/video 346 are analyzed (e.g., interpreted by medical personnel as part of an exemplary map interpretation layer) at block 348 to determine ROIs to be ablated at block 350. The combined maps/video 346 represent a spatio-temporal manifestation of the AF process 316 which can be easily visualized and interpreted, facilitating an efficient and accurate process for determination of ROIs for ablation. Determined ROIs may be represented (e.g., displayed), for example, by color, by 3-D contour on a 4-D map, by icons (e.g., dynamically changing icons), etc.

In some embodiments, both the combined driver/perpetuator map 334 and the combined maps/video 346 are used to determine ROIs for ablation at block 350. In some embodiments either the combined driver/perpetuator map 334 or the combined maps/video 346 are used to determine ROIs for ablation at block 350. For example, the combined driver/perpetuator map 334 can be used to determine ROIs for ablation at block 350 without using (e.g., viewing, analyzing) the combined maps/video 346.

In some embodiments, the quality map 332 is also used in combination with the combined driver/perpetuator map 334 and/or the combined maps/video 346 to determine ROIs for ablation at block 350. The quality map 332 is used to determine the trustworthiness of the generated maps (e.g., driver map 328, perpetuator map 330 and driver/perpetuator map 334) related to AF substrate 314 and the generated maps (e.g., activation/wave maps 336, CV maps 338, fraction maps 340, voltage maps 342 and block maps 344) related to the AF process 316 parameters. If the quality of the quality map is low, the generated maps are less trusted and appointing an ablation ROI (350) must be regarded with an increase level of care (e.g., by a physician) compared to when the quality map indicates high quality signals (IC ECGs) as the basis for the generated maps.

In some embodiments, determining ROIs for ablation at block 350 includes appointing or selecting one or more ablation sites for use in determining one or more ROIs for ablation. For example, ablation sites may be appointed or selected from driver evidence and perpetuator evidence (e.g., determined from the driver map 328, the perpetuator map 330 or the combined driver/perpetuator map 334) and ROIs may be determined based on the appointed sites.

The maps and mapping techniques disclosed herein potentially: (i) reduce AF map analysis training time; (ii) reduce time to determine ROIs for ablation; (iii) facilitate efficient interpretation of AF maps; and (iv) increase ablation success rates for ablation aimed at isolation and extinguishing of drivers, path lengthening, slowing of re-entry circuits, fibrillatory conduction and fractionated potentials.

Figure 5:
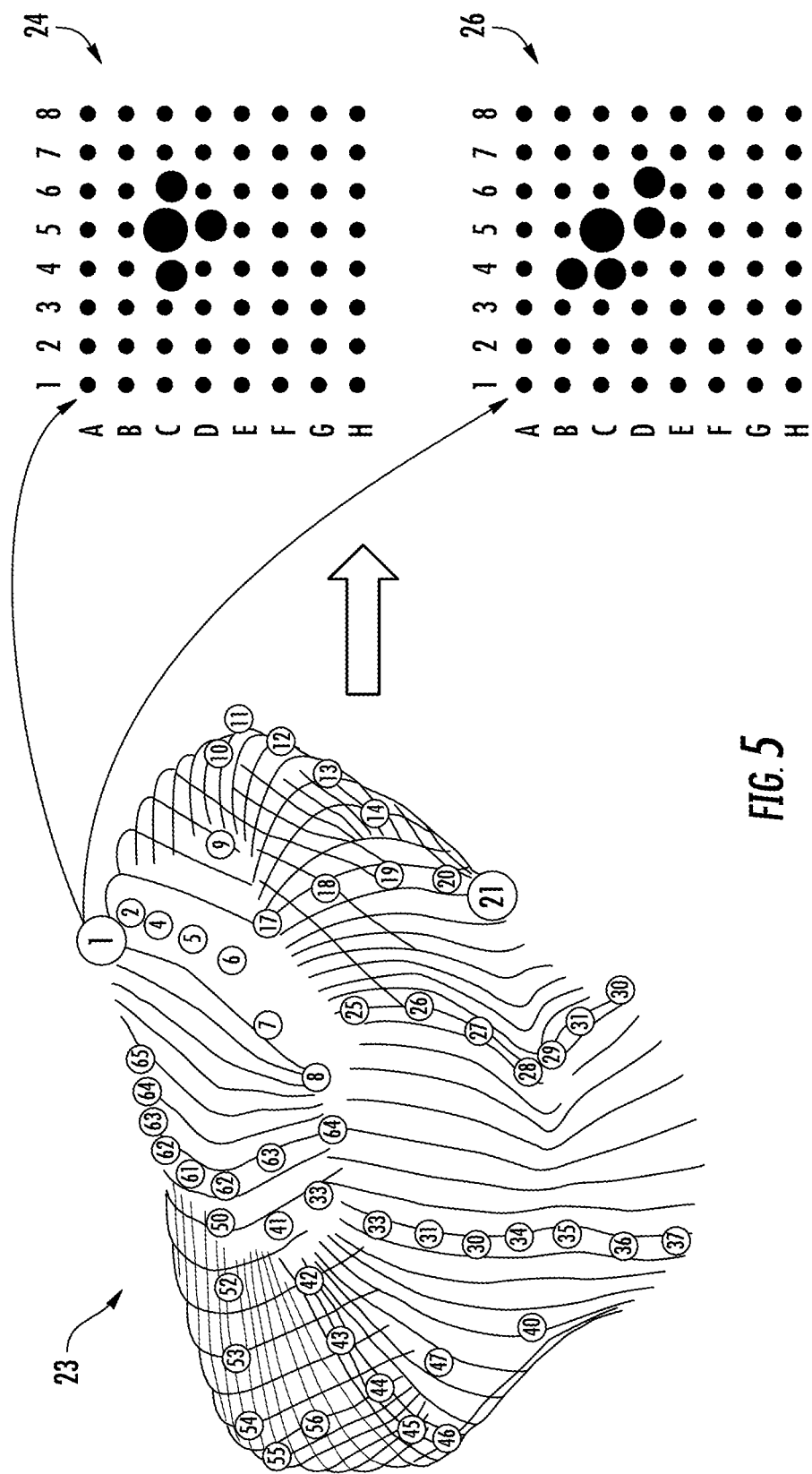
FIG. 5 is a schematic illustration of hypothetical data acquired from a subject during an episode of AF, in accordance with some embodiments of the present invention.
Figure 6:
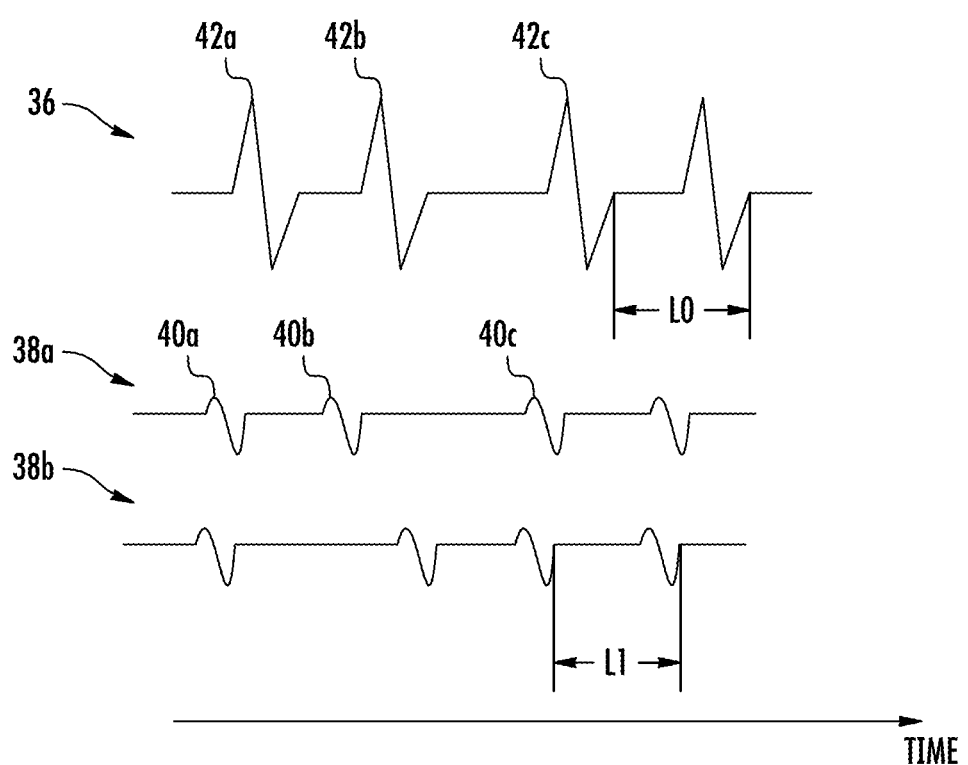
FIG. 6 is a schematic illustration of hypothetical ECG signals acquired from a subject during an episode of AF.

As mentioned above, AF may be treated by ablating the focal sources of the abnormal electrical discharges that cause the fibrillation. Embodiments of the present invention facilitate such treatment, by identifying the focal sources. Methods for performing such identification of focal sources are illustrated in FIGS. 4-6.

Figure 4:
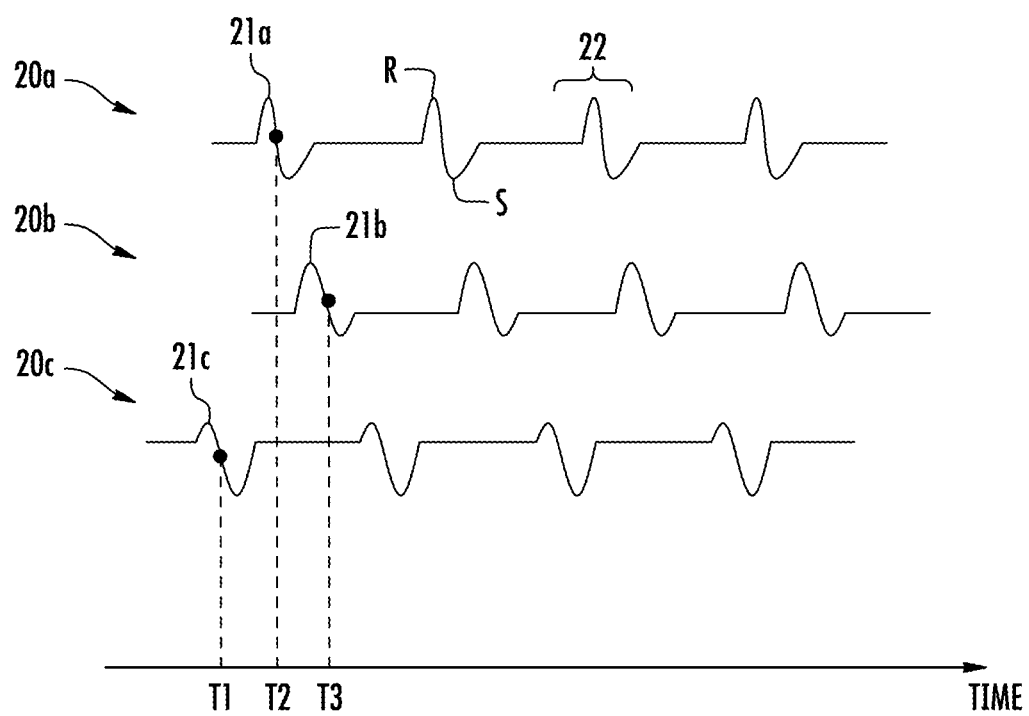
FIG. 4 shows hypothetical intracardiac electrocardiogram (ECG) signals acquired from a subject during an episode of AF.

FIG. 4 shows an embodiment of a method for identifying focal sources in which hypothetical intracardiac electrocardiogram (ECG) signals 20a, 20b, and 20c are acquired from a subject during an episode of AF. This method can be referred to as an "RS-based method". Signals 20a-c may be acquired, for example, by respective electrodes in contact with neighboring regions of cardiac tissue of the subject. In practice, many (e.g., tens or hundreds) of such signal-acquiring electrodes may be distributed over the tissue to yield a "mapping" of the tissue.

Each of the signals in FIG. 4 comprises a sequence of R-S complexes 22, each R-S complex comprising an R wave, labeled "R" in the figure, followed by an S wave, labeled "S" in the figure. (It is noted that the hypothetical signals are schematically shown in FIG. 4 for sake of illustration, and do not necessarily include the level of detail that would normally be observed in actual intracardiac ECG signals.)

An ECG signal from a focal source of AF exhibits S waves that are much larger in magnitude than the R waves of the ECG signal. As the distance from the focal source increases, the R waves become larger, relative to the S waves. Accordingly, the magnitudes of the R waves and S waves in the hypothetical data shown in FIG. 4 indicate that the electrode that acquired signal 20c may be located at, or very near to, a focal source. The electrode that acquired signal 20a (which has R waves and S waves of approximately equal magnitude) may be next-closest to the focal source, followed by the electrode that acquired signal 20b.

Over a small number of activation cycles (such as is shown in FIG. 4), the magnitudes of the R waves and S waves do not necessarily provide for identifying a focal source. Over a larger number of cycles, however, a signal that consistently, with relatively few exceptions, shows sufficiently strong S waves is indeed likely to be emanating from a focal source.

Embodiments of the present invention additionally use another method for locating focal sources. In accordance with this second method, the local activation time (LAT) for each of the R-S complexes is identified, by, for example, identifying the time at which the derivative of the R-S complex obtains its most negative value, between the R wave and the S wave. Since, during each activation cycle, the LAT of a focal source, by definition, precedes the LATs of adjacent areas of tissue, the LATs may be used to identify focal sources.

For example, FIG. 4 shows LATs of T1, T2, and T3 for the first R-S complexes of signals 20c, 20a, and 20b, respectively. Using, for example, wave-mapping techniques in which the waves are decomposed, into three distinct types: peripheral waves (waves entering the mapping area from outside), epcardial breakthrough waves (waves appearing at the epicardial surface inside the mapping area) and discontinuous conduction waves (waves starting at the lateral boundary of another fibrillation wave with a time delay of 13 to 40 ms), it may be ascertained that these three R-S complexes—complex 21a belonging to signal 20a, complex 21b belonging to signal 20b, and complex 21c belonging to signal 20c-belong to the same activation cycle. Therefore, the chronological ordering of T1, T2, and T3 indicates that the electrode that acquired signal 20c may be at, or very near to, a focal source; next-closest is the electrode that acquired signal 20a, followed by the electrode that acquired signal 20b.

Over a small number of activation cycles (such as is shown in FIG. 4), the ordering of activation times does not necessarily provide for identifying a focal source. Over a larger number of cycles, however, a signal that consistently, with relatively few exceptions, exhibits the earliest activation time relative to neighboring regions of tissue is indeed likely to be emanating from a focal source.

Although the latter, "LAT-based" method may identify focal sources with a reasonable degree of success, the method may fail in cases in which a particular focal source is outside the range of the electrode mapping. In such cases, the region of earliest activation recorded by the electrodes might be identified as a focal source, even though the actual focal source is nearby, outside the range of the electrode mapping. Furthermore, there is a risk that noise in the signals will lead to incorrect identification and/or ordering of the LATs, and thus, incorrect identification of focal sources.

Similarly, using only the "RS-based" method described above (which may also be referred to as "morphological analysis"), there is a risk that insufficient resolution in the electrode mapping may lead to a particular region being identified as a focal source, even though only a portion of the region is the actual focal source. Moreover, non-contact and noise in the signals may lead to improper measurement of the magnitudes of the R waves and S waves, and thus, incorrect identification of focal sources.

In light of the above, as further described below, the two methods are used in combination, thus allowing for identifying focal sources with a higher degree of confidence. For example, if a particular earliest-activation point identified by the LAT method does not exhibit a strong S wave, it may be deduced that the earliest-activation point is likely not a focal source. Consequently, in some cases, electrodes may be placed over additional regions of tissue near the earliest-activation point, in order to find the true focal source. Similarly, if a particular region shows a strong S wave but not enough earliest activations, it may be deduced that the region likely does not contain a focal source, or alternatively, the region may be mapped with greater resolution.

Reference is now made to FIG. 5, which is a schematic illustration of hypothetical data acquired from a subject during an episode of AF, in accordance with some embodiments of the present invention.

On the left side of FIG. 5 is a representation of a three-dimensional basket electrode assembly 23, which may be used to map cardiac tissue of a subject, as described above. Such a representation may be shown, for example, on a display, during a mapping procedure. The electrodes in assembly 23 are numbered 1 through 64. (Some of these numbers are not clearly shown in the figure.)

Based on ECG signals recorded by assembly 23, maps (or arrays), such as those shown on the right side of FIG. 5, may be constructed, and displayed on a display. For example, FIG. 5 shows an LAT-based map 24 and an RS-based map 26. Each of these maps translates the three-dimensional basket electrode assembly into a two-dimensional array, where each element in the array corresponds to a respective electrode. For example, electrode 1 in the assembly is mapped to element A1, electrode 2 to A2, electrode 9 to B1, etc. Such a layout typically allows the acquired data to be more easily visualized. (In some embodiments, a one-dimensional array may be shown, alternatively to a two-dimensional array.)

LAT-based map 24 represents, by differently-sized markers, the respective numbers of earliest activation cycles recorded by the electrodes during the mapping period. For example, a marker of size "10" might indicate that during the mapping period, the corresponding electrode recorded the ten earliest activations, i.e., ten activations that were earlier than the activations of all of the neighboring electrodes. Thus, for example, the relatively large marker C5 in map 24 indicates that the electrode corresponding to marker C5, that is electrode 21, recorded an earliest LAT a relatively large number of times. The relatively small size of marker A1, on the other hand, indicates that electrode 1 did not record a large number of earliest activations.

Analogously, RS-based map 26 represents, by differently sized markers, the respective average R-to-S ratios recorded by the electrodes, during the same mapping period (i.e., over the same sequence of activation cycles) on which map 24 is based. (An R-to-S ratio is the ratio of the absolute magnitude of the R wave to the absolute magnitude of the S wave.) A higher ratio is represented in map 26 by a smaller-sized marker; conversely, a lower ratio is represented by a larger-sized marker.

By correlating the maps with one another, specific markers that are relatively large in both of the maps may be identified, and thus, specific regions of interest may be identified. For example, markers C4, C5, and D5 are relatively large in both of the maps, and thus, the electrodes corresponding to these markers are likely to be near one or more focal sources. On the other hand, marker C6 is relatively large in map 24, but not in map 26; hence, the electrode corresponding to marker C6 is likely not a focal source. Hence, by correlating LAT-based map 24 with RS-based map 26 (i.e., by checking that potential focal sources identified in one of the maps are also identified in the other map), focal sources may be identified with a greater degree of confidence, relative to if only one of the maps were used. Such correlation may be done automatically by a processor, or manually, e.g., in response to viewing the two maps on a display.

It is noted that the scope of the present invention includes displaying maps 24 and 26 using any suitable system of representation. That is, any suitable type(s) of marker may be used, and any suitable property (e.g., color, texture, size) may be differentially set for the markers, alternatively or additionally to the size of the markers. Alternatively or additionally, LAT-indicative markers and/or RS-indicative markers may be shown on the representation of three-dimensional assembly 23, alternatively or additionally to being shown in a topological array.

In some cases of AF in which a plurality of focal sources are present, none of the focal sources is dominant. In other cases, however, at least one of the focal sources is a dominant focal source that primarily drives the arrhythmia, such that it is typically advantageous to identify the dominant focal source(s).

A case in which a dominant focal source is present is depicted in FIG. 6, which is a schematic illustration of hypothetical ECG signals acquired from a subject during an episode of AF. Signal 36 is a hypothetical arrhythmic signal acquired from the coronary sinus of a subject during an episode of AF. Signals 38a and 38b are hypothetical intracardiac ECG signals that were identified (e.g., using techniques described above) as emanating from respective focal sources of the subject.

In some embodiments, the dominant focal source is found (e.g., automatically, by a processor), by comparing the cycle lengths L1 of each of the focal-source signals with the temporally-corresponding cycle lengths L0 of the arrhythmic heartbeat signal. The focal source whose signal cycle-lengths correspond most closely to those of the heartbeat signal is deemed to be the dominant focal source. For example, in FIG. 6, the cycle lengths of signal 38a correspond more closely to those of signal 36 than do the cycle lengths of signal 38b. For example, the time between R-S complexes 40a and 40b in signal 38a is approximately equal to the time between R-S complexes 42a and 42b in signal 36, the time between R-S complexes 40b and 40c in signal 38a is approximately equal to the time between R-S complexes 42b and 42c in signal 36, etc. Therefore, the source of signal 38a is identified as the dominant focal source.

Although FIG. 6 shows a relatively simplistic case, it is noted that embodiments of the present invention may also be used to identify dominant focal sources in more complicated cases, such as where the focal sources are active at different times, and/or where multiple focal sources are present. For example, embodiments of the present invention may identify two or more focal sources that alternate with each other in driving the arrhythmia.

It should be understood that many variations are possible based on the disclosure herein. Although features and elements are described above in particular combinations, each feature or element can be used alone without the other features and elements or in various combinations with or without other features and elements.

Documents incorporated by reference in the present patent application are to be considered an integral part of the application except that to the extent any terms are defined in these incorporated documents in a manner that conflicts with the definitions made explicitly or implicitly in the present specification, only the definitions in the present specification should be considered.

The methods provided include implementation in a general purpose computer, a processor, or a processor core. Suitable processors include, by way of example, a general purpose processor, a special purpose processor, a conventional processor, a digital signal processor (DSP), a plurality of microprocessors, one or more microprocessors in association with a DSP core, a controller, a microcontroller, Application Specific Integrated Circuits (ASICs), Field Programmable Gate Arrays (FPGAs) circuits, any other type of integrated circuit (IC), and/or a state machine. Such processors can be manufactured by configuring a manufacturing process using the results of processed hardware description language (HDL) instructions and other intermediary data including netlists (such instructions capable of being stored on a computer readable media). The results of such processing can be maskworks that are then used in a semiconductor manufacturing process to manufacture a processor which implements method described herein.

The methods or flow charts provided herein can be implemented in a computer program, software, or firmware incorporated in a non-transitory computer-readable storage medium for execution by a general purpose computer or a processor. Examples of non-transitory computer-readable storage mediums include a ROM, a random access memory (RAM), a register, cache memory, semiconductor memory devices, magnetic media such as internal hard disks and removable disks, magneto-optical media, and optical media such as CD-ROM disks, and digital versatile disks (DVDs).

What is claimed is:

1. A method for determining atrial fibrillation regions of interest to be ablated comprising:
    acquiring, via a plurality of sensors, electro-cardiogram (ECG) signals over time, each ECG signal acquired via one of the plurality of sensors and representing electrical activity of one of a plurality of different areas of a heart, each ECG signal comprising at least an R wave and an S wave;
    determining local activation times (LATs) of each ECG signal, each LAT of a respective ECG signal corresponding to acquired electrical activity at a different point in time;
    identifying a plurality of LATs determined to be part of a same cardiac activation cycle;
    generating first mapping information for visually indicating, at locations on a local activation time (LAT) map for each ECG signal, a number of instances, during a period of time that includes multiple cardiac activation cycles, in which at least one of the plurality of LATs is a chronologically earliest LAT; and
    generating second mapping information for visually indicating, at locations on an R-S map corresponding to the same locations on the LAT map, sizes of R-to-S ratios for each ECG signal in the period of time that includes multiple cardiac activation cycles, each R-to-S ratio comprising a ratio of a magnitude of the R wave to a magnitude of the S wave,
    wherein, potential focal sources of activation of the heart are identified based on the visually indicated number of times at each location on the LAT map and the visually indicated sizes of the R-to-S ratios at each corresponding location on the R-S map.

2. The method of claim 1, wherein determining the LATs further comprises:
    calculating a derivative for each of the R-S ratios; and
    identifying the chronologically earliest LAT having a largest negative value of the calculated derivative of the R-S ratio.

3. The method of claim 2, wherein generating second mapping information further comprises:
    determining, from the plurality of ECG signals, a strongest ECG signal having a largest difference between the magnitude of the R wave and the magnitude of the S wave, and determining a location of the sensor having the strongest ECG signal, wherein at least one of the focal sources is identified as the location of the sensor having the strongest ECG signal and the chronologically earliest LAT.

4. The method of claim 3,
    wherein the number of instances at each location on the LAT map and the sizes of the R-to-S ratios on the R-S map are visually indicated by one of color, texture and size.

5. The method of claim 1, further comprising determining a dominant focal source from the identified focal sources.

6. The method of claim 5, determining the dominant focal source further comprises:
    comparing cycle lengths of each of the identified focal sources with temporally-corresponding cycle lengths of a previously acquired signal; and
    determining the dominant focal source as the identified focal source having the cycle length corresponding most closely to the temporally-corresponding cycle length of the previously acquired signal.

7. The method of claim 1, wherein
    the LAT map comprises a first array of a number of columns and a number of rows, the first array visually indicating, for each electrode, a number of early activation times at a location on the first array, and
    the R-S map comprises a second array of a same number of columns and a same number rows as the first array, the second array visually indicating, for each electrode, the sizes of R-to-S ratios at the corresponding locations.

8. A system for determining atrial fibrillation regions of interest to be ablated comprising:
    a plurality of sensors each configured to acquire one of a plurality of electro-cardiogram (ECG) signals over time representing electrical activity of one of a plurality of different areas of a heart, each ECG signal comprising an R wave and an S wave; and
    a processing device comprising one or more processors configured to:
    determine local activation times (LATs) of each ECG signal, each LAT of a respective ECG signal corresponding to acquired electrical activity at a different point in time;
    identify a plurality of LATs determined to be part of a same cardiac activation cycle;

generate first mapping information for visually indicating, at locations on a local activation time (LAT) map for each ECG signal, a number of instances, over a period of time that includes multiple cardiac activation cycles, in which at least one of the plurality of LATs is a chronologically earliest LAT; and generate second mapping information for visually indicating, at locations on an R-S map corresponding to the same locations on the LAT map, sizes of R-to-S ratios for each ECG signal in the period of time that includes multiple cardiac activation cycles, each R-to-S ratio comprising a ratio of a magnitude of the R wave to a magnitude of the S wave, wherein potential focal sources of activation of the heart are identified based on the visually indicated number of times at each location on the LAT map and the visually indicated sizes of the R-to-S ratios at each corresponding location on the R-S map.

9. The system of claim 8, wherein the processing device is further configured to:

calculate a derivative for each of the R-S ratios; and identify the chronologically earliest LAT having a largest negative value of the calculated derivative of the R-S ratio.

10. The system of claim 9, wherein the processing device is further configured to:

determine, from the plurality of ECG signals, a strongest ECG signal having a largest difference between the magnitude of the R wave and the magnitude of the S wave, and determining a location of the sensor having the strongest ECG signal, wherein at least one of the focal sources is identified as the location of the sensor having the strongest ECG signal and the chronologically earliest LAT.

11. The system of claim 10, wherein the number of instances at each location on the LAT map and the sizes of the R-to-S ratios on the R-S map are visually indicated by one of color, texture and size.

12. The system of claim 8, wherein the processing device is further configured to determine a dominant focal source from the identified focal sources.

13. The system of claim 12, wherein the processing device is further configured to:

compare cycle lengths of each of the identified focal sources with temporally-corresponding cycle lengths of a previously acquired signal; and determine the dominant focal source as the identified focal source having the cycle length corresponding most closely to the temporally-corresponding cycle length of the previously acquired signal.

14. A non-transitory computer readable storage medium in which computer program instructions are stored for determining atrial fibrillation regions of interest to be ablated, which instructions, when executed by a computer, cause the computer to perform the steps of:

acquiring, via a plurality of sensors, electro-cardiogram (ECG) signals over time, each ECG signal acquired via one of the plurality of sensors and representing electrical activity of one of a plurality of different areas of a heart, each ECG signal comprising at least an R wave and an S wave;

determining local activation times (LATs) of each ECG signal, each LAT of a respective ECG signal corresponding to acquired electrical activity at a different point in time;

identifying a plurality of LATs determined to be part of a same cardiac activation cycle;

generating first mapping information for visually indicating, at locations on a local activation time (LAT) map for each ECG signal, a number of instances, over a period of time that includes multiple cardiac activation cycles, in which at least one of the plurality of LATs is a chronologically earliest LAT; and generating second mapping information for visually indicating, at locations on an R-S map corresponding to the same locations on the LAT map, sizes of R-to-S ratios for each ECG signal in the period of time that includes multiple cardiac activation cycles, each R-to-S ratio comprising a ratio of a magnitude of the R wave to a magnitude of the S wave, wherein, potential focal sources of activation of the heart are identified based on the visually indicated number of times at each location on the LAT map and the visually indicated sizes of the R-to-S ratios at each corresponding location on the R-S map.

15. The computer readable storage medium of claim 14, wherein determining the LATs further comprises:

calculating a derivative for each of the R-S ratios; and identifying the chronologically earliest LAT having a largest negative value of the calculated derivative of the R-S ratio.

16. The computer readable storage medium of claim 15, wherein generating second mapping information further comprises:

determining, from the plurality of ECG signals, a strongest ECG signal having a largest difference between the magnitude of the R wave and the magnitude of the S wave, and determining a location of the sensor having the strongest ECG signal, wherein at least one of the focal sources is identified as the location of the sensor having the strongest ECG signal and the chronologically earliest LAT.

17. The computer readable storage medium of claim 16, wherein the number of instances at each location on the LAT map and the sizes of the R-to-S ratios on the R-S map are visually indicated by one of color, texture and size.

18. The computer readable storage medium of claim 14, further comprising determining a dominant focal source from the identified focal sources.

19. The computer readable storage medium of claim 18, wherein determining a dominant focal source further comprises:

comparing cycle lengths of each of the identified focal sources with temporally-corresponding cycle lengths of a previously acquired signal; and determining the dominant focal source as the identified focal source having the cycle length corresponding most closely to the temporally-corresponding cycle length of the previously acquired signal.

* * * * *

UNITED STATES PATENT AND TRADEMARK OFFICE
CERTIFICATE OF CORRECTION

| | |
|---|---|
| PATENT NO. | : 11,771,359 B2 |
| APPLICATION NO. | : 17/231612 |
| DATED | : October 3, 2023 |
| INVENTOR(S) | : Roy Urman et al. |

It is certified that error appears in the above-identified patent and that said Letters Patent is hereby corrected as shown below:

On the Title Page
On Page 2, Item (56), under "OTHER PUBLICATIONS", in Column 2, Line 1, delete "long standing" and insert -- long-standing --, therefor.
On Page 2, Item (56), under "OTHER PUBLICATIONS", in Column 2, Line 18, delete "Longstanding" and insert -- Long-Standing --, therefor.
On Page 2, Item (56), under "OTHER PUBLICATIONS", in Column 2, Line 34, delete "No. 171516255." and insert -- No. 17151625.5. --, therefor.

In the Specification
In Column 1, Line 37, delete "relates" and insert -- relates to --, therefor.
In Column 3, Line 46, delete "herein; and" and insert -- herein; --, therefor.
In Column 3, Line 49, delete "embodiment." and insert -- embodiment; --, therefor.
In Column 3, Line 52, delete "AF." and insert -- AF; --, therefor.
In Column 3, Line 55, delete "invention." and insert -- invention; and --, therefor.
In Column 3, Line 63, delete "guided up" and insert -- guiding it up --, therefor.
In Column 10, Line 40, delete "epcardial" and insert -- epicardial --, therefor.

In the Claims
In Column 14, Line 49, in Claim 7, delete "number rows" and insert -- number of rows --, therefor.

Signed and Sealed this
Thirteenth Day of February, 2024

Katherine Kelly Vidal
*Director of the United States Patent and Trademark Office*